(12) United States Patent
Nguyen et al.

(10) Patent No.: US 8,779,781 B2
(45) Date of Patent: Jul. 15, 2014

(54) CAPACITIVE SENSOR, INTEGRATED CIRCUIT, ELECTRONIC DEVICE AND METHOD

(75) Inventors: Viet Hoang Nguyen, Leuven (BE); Roel Daamen, Herkenbosch (NL); Axel Nackaerts, Heverlee (BE); Pascal Bancken, Opwijk (BE)

(73) Assignee: NXP, B.V., Eindhoven (NL)

( * ) Notice: Subject to any disclaimer, the term of this patent is extended or adjusted under 35 U.S.C. 154(b) by 183 days.

(21) Appl. No.: 13/438,716

(22) Filed: Apr. 3, 2012

(65) Prior Publication Data

US 2012/0256645 A1    Oct. 11, 2012

(30) Foreign Application Priority Data

Apr. 8, 2011    (EP) ..................................... 11161723

(51) Int. Cl.
*G01R 27/26*    (2006.01)

(52) U.S. Cl.
USPC ......................................................... 324/679

(58) Field of Classification Search
USPC ............ 324/672–684, 600, 709–718; 73/861, 73/304 C
See application file for complete search history.

(56) References Cited

U.S. PATENT DOCUMENTS

| | | | |
|---|---|---|---|
| 6,744,258 B2 * | 6/2004 | Ishio et al. | ..................... 324/548 |
| 8,096,182 B2 * | 1/2012 | Lin et al. | ..................... 73/514.32 |
| 8,429,981 B2 * | 4/2013 | Grosjean et al. | ................. 73/771 |
| 2003/0011378 A1 * | 1/2003 | Ishio et al. | ..................... 324/519 |
| 2007/0200718 A1 | 8/2007 | Veerasamy | |

FOREIGN PATENT DOCUMENTS

WO    2005/095936 A1    10/2005

OTHER PUBLICATIONS

Extended European Search Report for EP Patent Appln. No. 11161723.9 (Aug. 16, 2011).

* cited by examiner

*Primary Examiner* — Melissa Koval
*Assistant Examiner* — Trung Nguyen

(57) ABSTRACT

A sensor for sensing an analyte includes capacitive elements, each having a pair of electrodes separated by a dielectric wherein the dielectric constant of the dielectric of at least one of the capacitive elements is sensitive to the analyte, the sensor further including a comparator adapted to compare a selected set of capacitive elements against a reference signal and to generate a comparison result signal, and a controller for iteratively selecting the set in response to the comparison result signal, wherein the sensor is arranged to produce a digitized output signal indicative of the sensed level of the analyte of interest. An IC comprising such a sensor, an electronic device comprising such an IC and a method of determining a level of an analyte of interest using such a sensor are also disclosed.

13 Claims, 4 Drawing Sheets

CAPACITIVE SENSOR, INTEGRATED CIRCUIT, ELECTRONIC DEVICE AND METHOD

FIELD OF THE INVENTION

Figure 1:
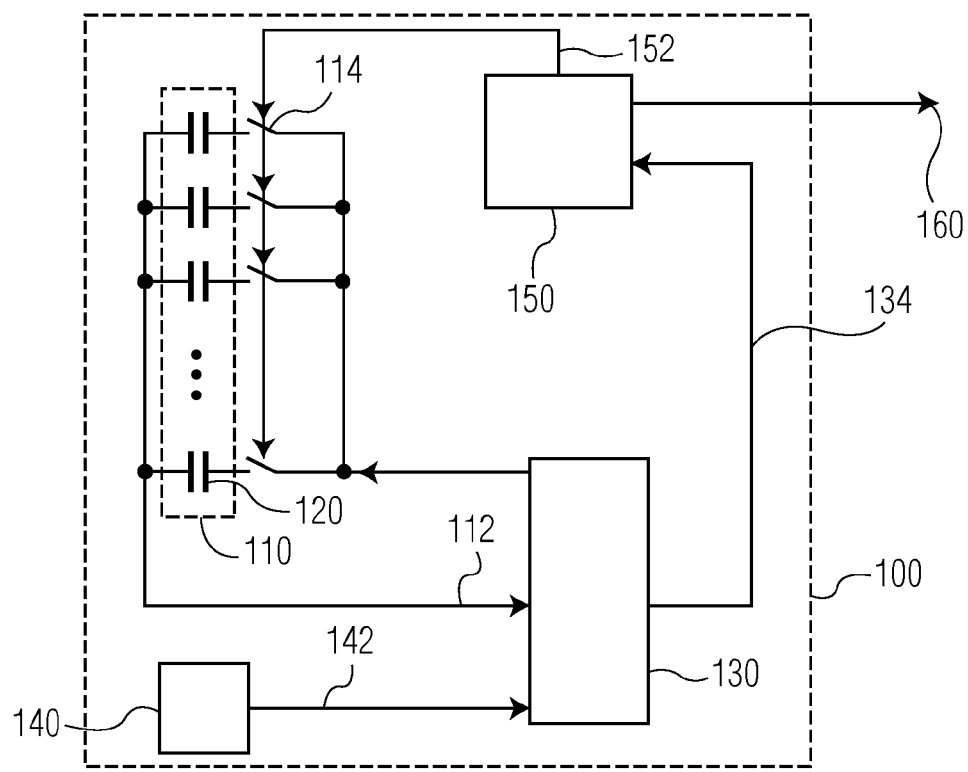

The present invention relates to sensor for sensing an analyte of interest, the sensor comprising a capacitive sensing element comprising a pair of electrodes separated by a dielectric medium wherein the dielectric constant of the dielectric medium is sensitive to the analyte of interest.

The present invention further relates to an integrated circuit (IC) comprising such a sensor.

The present invention yet further relates to an electronic device comprising such an IC.

The present invention still further relates to a method of determining a level of the analyte of interest using such a sensor.

BACKGROUND OF THE INVENTION

Nowadays, integrated circuits (ICs) may comprise capacitive sensors such as a moisture-sensitive sensor, e.g. a relative humidity (RH) sensor or a liquid immersion detection sensor. The capacitive sensing element of such a sensor typically comprises a pair of electrodes, i.e. capacitor plates separated by a dielectric medium, wherein the dielectric constant of the dielectric medium is sensitive to a level of the analyte of interest, e.g. moisture. The analyte of interest is typically absorbed by the dielectric medium, which causes the dielectric constant of the dielectric medium to change, thereby changing the overall capacitance of the capacitive sensing element. Hence, the determination of the capacitance of the capacitive sensing element represents an indication of the levels of the analyte of interest to which the capacitive sensing element has been exposed.

Such sensors may be included in the IC design for a number of reasons. For instance, such a sensor may be included in the ICs to determine whether a malfunctioning IC that has been returned, e.g. to its manufacturer, has been damaged by exposure to moisture, e.g. an immersion event, or whether the IC itself is faulty. The determination of such external influences as a cause of malfunction may be of crucial importance to deciding whether or not the customer returning the IC or an electronic device including the IC is entitled to a warranty claim on the device, as misuse such as the aforementioned immersion event typically invalidates the warranty.

Alternatively, such a sensor may be part of the functionality of an IC. There is for instance a trend towards providing near-field communication ICs such as radio-frequency (RF) identification (ID) chips with a range of sensors, such as temperature sensors, ambient light sensors, mechanical shock sensors, liquid immersion sensors, humidity sensors, $CO_2$ sensors, $O_2$ sensors, pH sensors and ethylene sensors, which for instance may be used to monitor the ambient conditions of a product tagged with the chip such that product quality control can be achieved by monitoring the sensor readings of the chip.

It is particularly attractive to integrate at least some of these sensors in the back-end of the manufacturing process of an IC, such as in or on the metallization stack, as this facilitates a cost-effective route to such integration due to the fact that such integration can be achieved with minimal alteration to the process flow.

A drawback of such capacitive sensors is the relatively slow response time. There are two factors contributing to this slowness. Firstly, the limited diffusion rate of the analyte into the dielectric medium of the sensing element causes an intrinsic delay, and secondly the generated measurement signal is an analog signal, for which the conversion into the digital domain adds another processing step and an associated delay.

SUMMARY OF THE INVENTION

The present invention seeks to provide a sensor that has an improved response speed.

The present invention further seeks to provide an IC including such a sensor.

The present invention yet further seeks to provide an electronic device including such an IC.

The present invention still further seeks to provide a method of determining the level of an analyte of interest using such a sensor.

In accordance with a first aspect of the present invention, there is provided a sensor for sensing an analyte of interest, the sensor comprising a plurality of capacitive elements, each capacitive element comprising a pair of electrodes separated by a dielectric medium wherein the dielectric constant of the dielectric medium of at least one of the capacitive elements is sensitive to the analyte of interest, the sensor further comprising a comparator adapted to compare a selected set of said capacitive elements against a reference signal and to generate a comparison result signal, and a controller for selecting said set and for iteratively updating a digitized value indicative of the sensed level of the analyte of interest in response to said comparison result signal, wherein the sensor is arranged to produce a digitized output signal indicative of the sensed level of the analyte of interest.

The present invention is based on the realization that by inclusion of at least one sensing capacitor in the sensor signal digitization stage, the generation of the digitized sensing signal can be produced more quickly compared to prior art arrangements in which a separate analog-to-digital converter was used for the generation of the digitized sensing signal. In addition, the integration of the at least one sensing capacitor in the sensor signal digitization stage facilitates a reduction in the overall size of the sensor, thus reducing manufacturing cost.

In an embodiment, the dielectric medium of each of said capacitive elements has a dielectric constant dependent on a concentration of the analyte of interest in said medium, and wherein the controller is configured to select said subset such that the overall capacity of the subset remains constant. In other words, the number of analyte-sensitive capacitive elements included in the sensor arrangement inversely scales with the level of the analyte of interest, e.g. moisture, as increasing moisture levels tend to increase the dielectric constant of the dielectric medium, thereby increasing the capacitance C of each individual capacitive element in accordance with $C=\in A/d$, in which $\in$ is the dielectric constant of the dielectric medium separating the electrodes, A is the area of the electrodes and d is the separation distance between the electrodes. Hence, the determination of the number of capacitive elements required to maintain a constant capacitance of the sensor can be directly translated to a level of the analyte of interest without requiring a separate analog to digital conversion stage.

In an embodiment, the plurality of capacitive elements comprises a first group of capacitive elements each having a first maximum capacity and a second group of capacitive elements each having a maximum capacity that is a multiple of the first maximum capacity. Such a multiple may for instance be a factor 10 such that by identification of how many capacitive elements of each group have been included in the sensor arrangement the level of the analyte of interest can be derived. This has the advantage that a smaller number of capacitive elements is required to obtain an accurate digitized sensor reading.

In an alternative embodiment, said plurality of capacitive elements defines a charge-scaling digital-to-analog converter (DAC), wherein the plurality of capacitive elements comprises a single capacitive element having a dielectric medium with a dielectric constant sensitive to a level of the analyte of interest, said single capacitive element defining the most significant bit of the digital-to-analog converter in an analog to digital conversion mode of the sensor, said plurality of capacitive sensing elements further comprising a further capacitive element having a dielectric medium with dielectric constant insensitive to the analyte of interest, said further capacitive element defining the most significant bit of the digital analog converter in a programming mode of the sensor; and wherein the controller comprises a successive approximation register for providing a digital code.

In this embodiment, the sensor is essentially integrated in a successive approximation analog to digital converter (ADC) which design has been altered in that during operation the charge programmed in the charge-scaling DAC is not compared against an input signal but against the reference signal, such that the replacement of the further capacitive element with the single capacitive element leads to a charge redistribution over the capacitive elements forming the charge-scaling DAC. The amount of redistributed charge is determined by the actual capacitance of the single capacitive element, which in turn is a function of the levels of the analyte in the dielectric medium of the single capacitive element, such that the successive approximation code generated in the analog-to-digital conversion stage is directly correlated to this analyte level.

In an embodiment, said capacitive elements may have a common electrode. This further reduces the complexity of the sensor design, thus further reducing manufacturing cost.

The sensor of the present invention may be advantageously included into an IC, wherein said capacitive elements are formed in or on the metallization stack of the integrated circuit. This has the advantage that the sensor functionality may be added to the IC at limited additional cost as the manufacturing process such as a CMOS process does not need to be (significantly) altered to accommodate the manufacture of the capacitive elements in the back end of the manufacturing process.

At least one of the electrodes of said capacitive elements may be formed in a metal layer of the metallization stack. Alternatively, in case the circuit elements underneath the metallization layer need to be protected from exposure to the analyte of interest, e.g. in the case of the sensor being a liquid immersion sensor, the capacitive elements may be formed on said metallization stack, said integrated circuit further comprising a moisture barrier layer, e.g. a $Ta_2O_5$ layer, between the capacitive sensing elements and the metallization stack.

The IC may be integrated into an electronic device such as a mobile communication device, e.g. a mobile phone, personal digital assistant, and so on.

In accordance with another aspect of the present invention, there is provided a method of determining a level of an analyte of interest, comprising providing a plurality of capacitive elements, each capacitive element comprising a pair of electrodes separated by a dielectric medium wherein the dielectric constant of the dielectric medium of at least one of the capacitive elements is sensitive to the analyte of interest; comparing said selected set of said capacitive elements against a reference signal and generating a comparison result signal; iteratively selecting said set in response to said comparison result signal; and generating a digitized signal indicative of the determined level of said analyte following completion of said iteration. This has the advantage that a digitized representation of the measured level of the analyte of interest can be generated without requiring a separate ADC.

In an embodiment, the dielectric constant of the dielectric medium of each of said capacitive elements is sensitive to the analyte of interest; said step of iteratively selecting said set comprises adjusting the number of capacitive elements in said set until said comparison result signal indicates a match between the aggregate capacitance of the capacitive elements in said set and the reference signal; and said step of generating the digitized signal comprises generating a signal indicative of the number of selected capacitive elements following completion of said iteration.

In an alternative embodiment, the dielectric constant of the dielectric medium of a single one of said capacitive elements is sensitive to the analyte of interest; the plurality of capacitive elements defines a charge scaling digital-to-analog converter including said single capacitive element as the most significant bit in a digital to analog conversion mode and a further capacitive element having a dielectric medium with a dielectric constant insensitive to the analyte of interest as the most significant bit in a programming mode; the method further comprises programming the digital-to-analog converter including the further capacitive element with a reference voltage in said programming mode; reconfiguring the digital-to-analog converter by replacing the further capacitive element with said single capacitive element; the step of iteratively selecting said set comprises sequentially selecting a single capacitive element of the digital to analog converter; and repeating the steps of comparing the charge stored on the selected capacitive element against the reference signal; and updating an successive approximation code in response to the generated comparison result signal until all capacitive elements of the digital-to-analog converter in the digital-to analog-conversion mode have been compared against the reference value; and wherein the step of generating the digitized signal comprises subsequently outputting the successive approximation code.

BRIEF DESCRIPTION OF THE EMBODIMENTS

Figure 2:
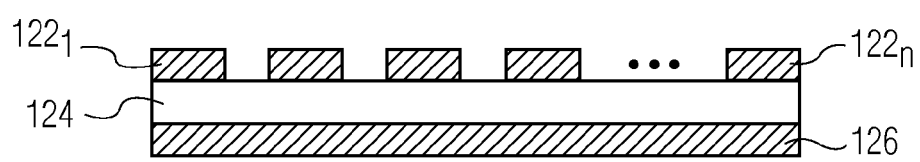
Figure 3:
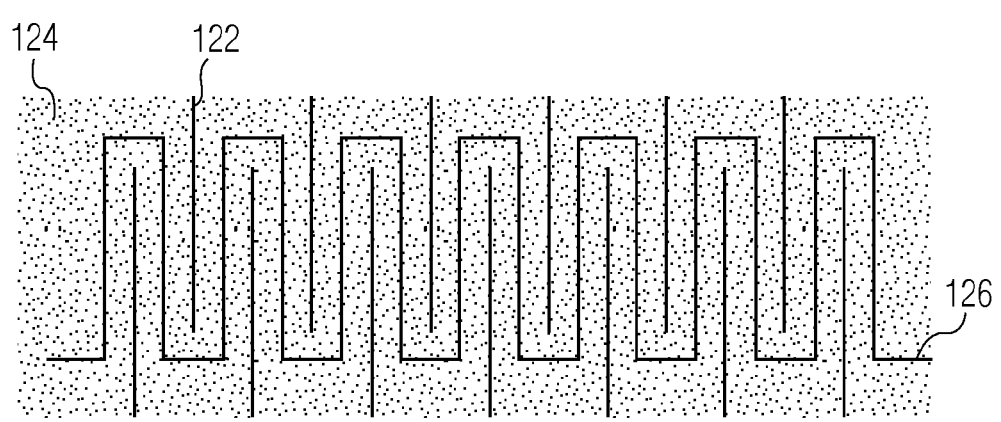
Figure 4:
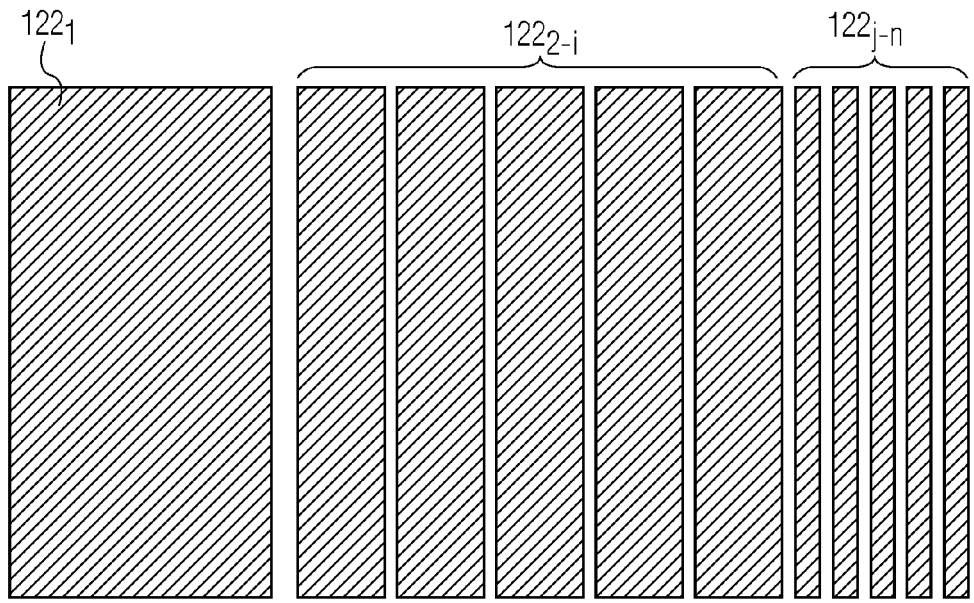
Figure 5:
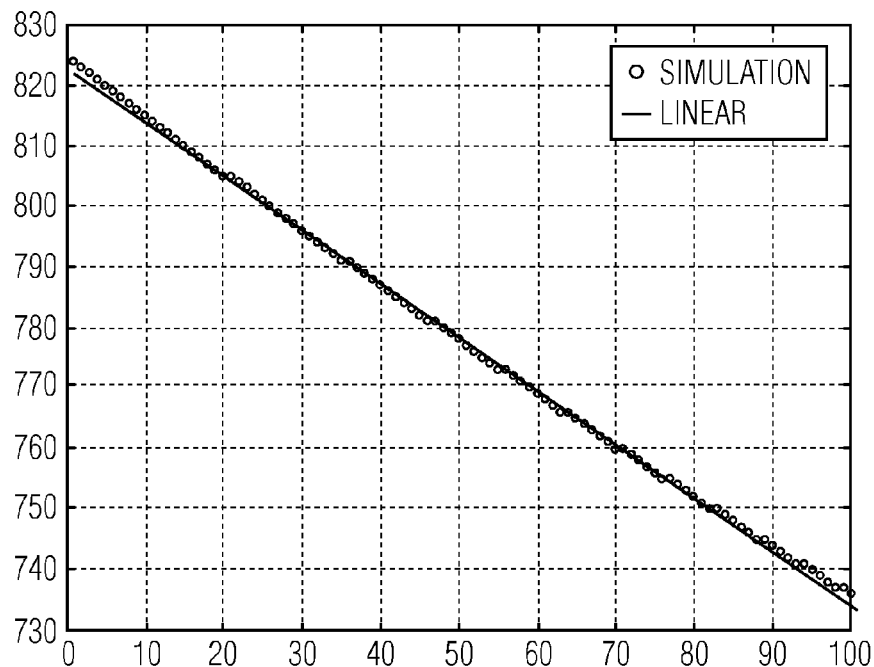
Figure 6:
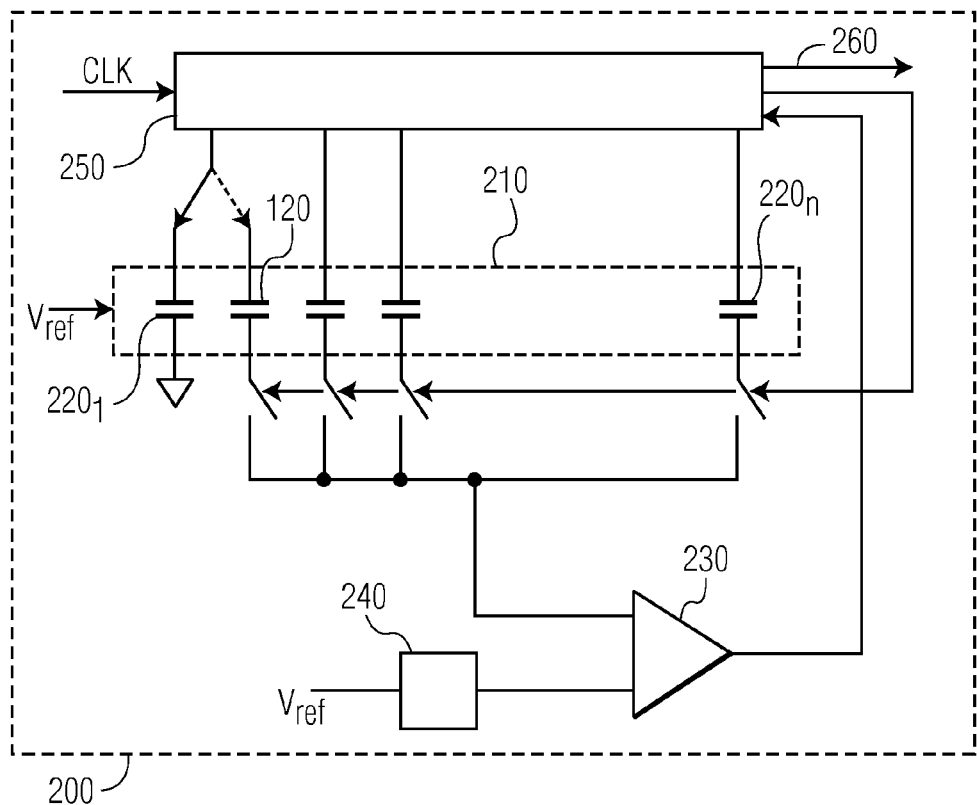
Figure 7:
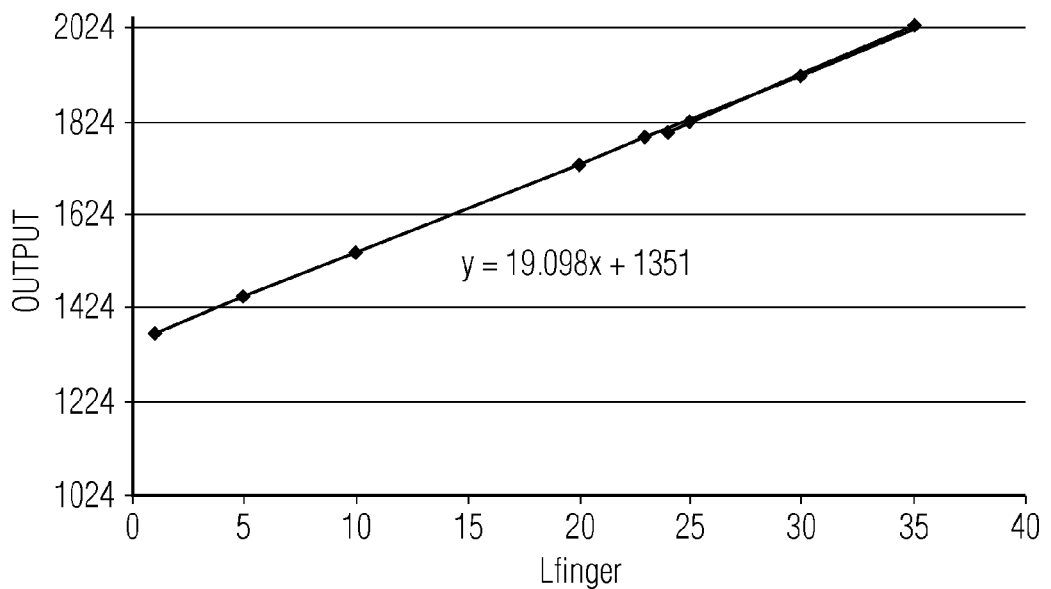
Figure 8:
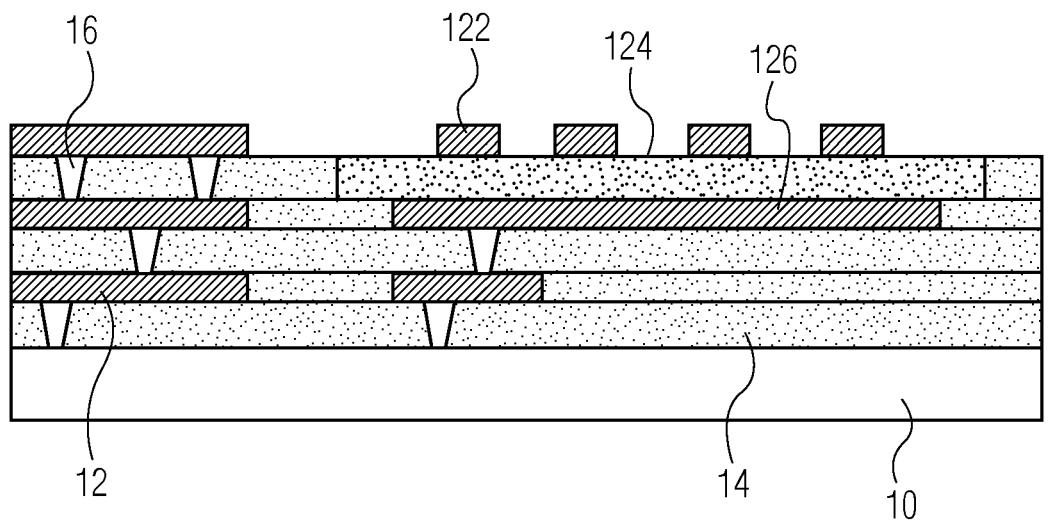

Embodiments of the invention are described in more detail and by way of non-limiting examples with reference to the accompanying drawings, wherein:

FIG. 1 schematically depicts a sensor according to an embodiment of the present invention;

FIG. 2 schematically depicts an aspect of a sensor according to an embodiment of the present invention;

FIG. 3 schematically depicts an aspect of a sensor according to another embodiment of the present invention;

FIG. 4 schematically depicts an aspect of a sensor according to yet another embodiment of the present invention;

FIG. 5 depicts a simulation result of the number of capacitors included in the sensing array as a function of relative humidity;

FIG. 6 schematically depicts a sensor according to an alternative embodiment of the present invention;

FIG. 7 depicts a simulation of the output signal of the sensor of FIG. 6 as a function of the capacitance of the most significant bit (MSB) capacitor; and FIG. 8 schematically depicts an example embodiment of an IC of the present invention.

DETAILED DESCRIPTION OF THE DRAWINGS

It should be understood that the Figures are merely schematic and are not drawn to scale. It should also be understood that the same reference numerals are used throughout the Figures to indicate the same or similar parts.

FIG. 1 schematically depicts a first embodiment of a capacitive sensor 100 of the present invention. The sensor 100 comprises a sensing array 110 comprising a plurality of capacitive elements 120, which may be arranged in any suitable layout. A non-limiting example of such a layout is shown in FIG. 2 in which the capacitive elements 120 share a common electrode 126 that is separated from the individual electrodes $122_{1-n}$ by a dielectric medium 124 that has a dielectric constant sensitive to the moisture levels absorbed by the dielectric medium. A non-limiting example of a suitable embodiment of the dielectric medium is polyimide although other suitable materials will be apparent to the skilled person. As shown in FIG. 3, the common electrode 126 may be a meandering electrode into which the individual electrodes $122_{1-n}$ of the separate capacitive elements 120 are interdigitated and separated from the common electrode 126 by the dielectric medium 124.

It is of course not necessary that the separate capacitors 126 share a common electrode; it is equally feasible that at least some of the capacitive elements 120 do not share an electrode. In the context of the present invention it should be understood that the phrase 'electrode' is intended to cover capacitor plates when used in reference to a capacitor.

Now, upon returning to FIG. 1, the sensor 100 further comprises a comparison circuit 130 that is adapted to compare the RC time of the sensing array 110 as provided on RC signal line 112 with a reference frequency generated by reference frequency source 140 on reference frequency signal line 142. The comparison circuit 130 may for instance comprise a frequency matching circuit for this purpose.

The sensor 100 further comprises a controller 150 for selecting the number of capacitive elements 120 to be included in the sensing array 110. To this end, the controller 150 may for instance be configured to provide enable signals to the individual switches 114, which may be implemented in any suitable manner, e.g. as MOSFETs. The controller 150 is responsive to the comparison result signal generated by the comparison circuit 130 in the following manner.

The overall capacitance C of the sensing array 110 is the sum of the individual capacitances of the capacitive elements 120 selected by the controller 150 to be included in the sensing array 120. The capacitance C is furthermore dependent of the exposure of the dielectric medium 124 to the analyte of interest, more specifically to the levels of the analyte of interest present in the dielectric medium 124, which will be assumed to be relative humidity for the remainder of this description by way of non-limiting example only; it should be understood that analytes other than moisture are equally feasible.

The RC time τ of the sensing array 110 can be expressed as $\tau = RC = 1/2\pi f_c$, in which R is the resistance of the RC signal line 112 and $f_c$ is the cut-off frequency of the capacitive sensing array 110. As C is dependent of the relative humidity and R is a constant (at least at first approximation), it can be seen that the RC time and cut-off frequency $f_c$ also depends of the actual relative humidity.

This principle is utilized by selecting the number of capacitive elements 120 to be included in the sensing array 110 such that the cut-off frequency $f_c$ is matched to the reference frequency provided by the reference frequency generation circuit 140, such that the following equation holds:

$$\text{Num\_cap} = \frac{1}{\frac{\Delta \varepsilon}{\varepsilon_{min}} \cdot \text{resolution}}$$

wherein Num_cap is the number of capacitive elements 120 included in the sensing array 110, $\Delta \varepsilon$ is the difference between dielectric constants of the dielectric material 124 at 100% and at 0% relative humidity, $\varepsilon_{min}$ is the minimum dielectric constant of the dielectric material 124, and resolution is the required resolution for the relative humidity measurement.

The comparison circuit 130 is adapted to calculate cut-off frequency $f_c$ of the sensing array 110 based on the measured RC time and to compare this cut-off frequency with the reference frequency from the reference frequency generator 140. Upon a mismatch between the cut-off frequency and the reference frequency, the comparison circuit 130 provides the controller 150 with an instruction over the instruction line 134 to incrementally increase of decrease the number of capacitive elements 120 in the sensing array 110. This iterative process is repeated until the comparison circuit 130 has determined that the cut-off frequency and the reference frequency are sufficiently matched.

Upon determining this matching, the number of capacitive elements 120 included in the sensing array 110 is representative for the relative humidity level that has been sensed by the sensor 100. Hence, the sensor 100, e.g. the controller 150 or the comparison circuit 130, may be adapted to output the number of capacitive elements 120 in the sensing array 110 on its output 160. To this end, the controller 150 or the comparison circuit 130 may comprise a counter for keeping track of the number of capacitive elements 120 included in the sensing array 110. Alternatively, the sensor 100 may comprise conversion means, e.g. a look-up table or alike, for converting the number of capacitive elements 120 included in the sensing array 110 into a relative humidity, in which case the output 160 may produce the actual value of the measured relative humidity. This allows for the output 160 to be produced in digital form without requiring a separate ADC.

At this point, it is noted that the minimum capacitance of the individual capacitive elements 120 may be chosen to be small, e.g. in the pF or even fF domain. It is not necessary that all the capacitive elements 120 have the same capacitance. It may in fact be advantageous to define two or more groups of capacitive elements 120 with different capacitances.

An example embodiment in which the capacitive elements 120 have different capacitances is shown in FIG. 4, in which the capacitive elements 120 have been grouped in different groups based on individual capacitance. The first group $122_1$ comprises a single capacitive element whereas second group $122_{2-i}$, and third group $122_{j-n}$ comprise a plurality of capacitive elements (i, j, n being positive integers with i<j<n), here shown to be 5 each by way of non-limiting example only. Each of these groups may contain any suitable number of capacitive elements and the sensor 100 may comprise any suitable number of such groups. For instance, the first group may contain capacitive elements each having a capacitance of 100 C, the second group may contain capacitive elements each having a capacitance of 10 C and the third group may contain capacitive elements each having a capacitance of 1 C (C being a unit capacitance). Assuming that each group comprises 10 of such capacitors, the controller 150 can define a sensing array 110 having a capacitance ranging from 1-1110 C using 30 capacitive elements only. In this example, a multiple of 10 is used to define the capacitances of the capacitive elements 120 between groups. It should be understood that any suitable multiplication factor, e.g. an integer or fractional factor, may be used.

FIG. 5 depicts a simulation result of the number of capacitors 120 each having a 11.5 femtoFarad (fF) capacitance and comprising a polyimide dielectric medium 124 included in the sensing array 110 (y-axis) as a function of relative humidity (RH, x-axis). The polyimide was shown to have a dielectric constant of 3.3 at 0% RH and 3.7 at 100 RH. As can be seen, to maintain a constant RC time of the sensing array 110, the number of capacitors 120 included in the sensing array 110 varied from 823 at RH=0% to 725 at RH=100%.

This demonstrates that not all capacitive elements 120 need to be selectable by the controller 150; it is equally feasible that the sensing array 110 comprises a first plurality of capacitive elements 120 that are permanently included in the sensing array, i.e. the number of capacitive elements 120 required to achieve the desired RC time at RH=100% and that the sensing array 110 further comprises a second plurality of capacitive elements 120 that can be added to the sensing array 110 by the controller 150 under control of the comparison circuit 130 as previously explained. The second plurality of capacitive elements 120 typically comprises a sufficient number of capacitive elements 120 to allow the generation of the desired RC time at RH=0%. This has the further advantage that the time required for the iterative process of matching the cutoff frequency of the sensing array 110 to the reference frequency is reduced, thus further reducing the amount of time required to determine the RH.

An alternative embodiment of the sensor of the present invention is shown in FIG. 6. Here, the sensor 200 takes the form of a charge-redistribution successive approximation ADC.

A conventional charge-redistribution successive approximation ADC which comprises a charge scaling DAC 210 including an array of capacitors 220$_1$-220$_n$, in which C220$_m$=2×C220$_{m+1}$ (m and n are positive integers with n>m), a comparator 230 for comparing the analog output of the charge scaling DAC 210 with an input voltage sampled in sample-and-hold circuit 240 and a controller 250 including a successive approximation register for generating a digital representation of the analog input voltage.

The operation of a charge-redistribution successive approximation ADC will now be briefly explained. As successive approximation ADCs are well-known per se a more detailed description has been omitted for the sake of brevity only.

In operation, the DA conversion is performed in four basic steps. The first three steps can be seen as the programming or initialization cycle of the ADC whereas the fourth and final step can be seen as the data conversion cycle of the ADC.

First, the capacitor array is completely discharged to the offset voltage of the comparator, $V_{OS}$. This step provides automatic offset cancellation, i.e. the offset voltage represents nothing but dead charge which cannot be redistributed over the capacitors 220$_{1-n}$. The successive approximation register is typically initialized such that the MSB is 1 and the less significant bits are 0, e.g. 1000 0000 0000 0000 for a 16-bit digital code.

Next, all of the capacitors 220 within the array 210 are switched to the input signal $V_{IN}$. The capacitors now have a charge equal to their respective capacitance times the input voltage minus the offset voltage upon each of them.

In the third step, the capacitors 220 are switched so that this charge is applied across the input of the comparator 230, creating a comparator input voltage equal to $-V_{IN}$.

Finally, the actual data conversion takes. First, the MSB capacitor 220$_1$ is switched to $V_{REF}$, which corresponds to the full-scale range of the ADC. Due to the binary-weighting of the array (i.e. C220$_m$=2×C220$_{m+1}$) the MSB capacitor 220$_1$ forms half of the capacitance of the total array 210. Consequently, the input voltage to the comparator 230 becomes $-v_{IN}+V_{REF}/2$. Subsequently, if $v_{IN}$ is greater than $V_{REF}/2$ then the comparator 230 outputs a digital 1 as the MSB, otherwise it outputs a digital 0 as the MSB. The controller 250 updates its successive approximation register accordingly. Each capacitor 220 is tested in the same manner until the comparator input voltage converges to the offset voltage, or at least as close as possible given the resolution of the DAC, after which the controller 250 produces the updated bit pattern of the successive approximation register on output 260.

Compared to such a conventional successive approximation DAC, the sensor 200 of the present invention is modified in the following manner. The design of the charge scaling DAC 210 is amended by the inclusion of a capacitive element 120, which is arranged in parallel with the MSB capacitor 220$_1$. The capacitive element 120 comprises a pair of electrodes separated by a dielectric medium having a dielectric constant dependent of the level of the analyte of interest, e.g. moisture, as previously explained. The other capacitors in the array 210, i.e. capacitors 220$_{1-n}$, have dielectrics with dielectric constants that are insensitive to changes in the analyte levels, e.g. are insensitive to relative humidity. In addition, the input signal of the sample-and-hold circuit 240 is simply the reference voltage. For this reason, the sample-and-hold circuit 240 may be omitted from the design of the sensor 200 if a sufficiently stable reference voltage can be produced.

During the programming or initialization phase, the MSB capacitor 220$_1$ is included in the charge scaling DAC 210 whereas the capacitive element 120 is not. The initialization of the charge scaling DAC 210 takes place as described above, including the above described initialization of the successive approximation register. Upon switching to the data conversion phase, the MSB capacitor 220$_1$ in the charge scaling DAC 210 is replaced by the capacitive element 120. This will cause a partial redistribution of the charge stored on capacitors 220$_{2-n}$ to the capacitive element 120. The amount of charge that is redistributed will depend on the capacitance of the capacitive element 120, which in turn will depend on the levels of the analyte of interest, e.g. moisture, absorbed in the dielectric medium 124 of the capacitive element 120.

Consequently, successive approximation code that is generated by the iterative or successive comparison of each of the capacitors 220$_{2-n}$ as well as capacitive element 120 against the reference voltage $V_{ref}$ by the comparator 230 will be indicative of the amount of charge redistributed from the capacitors 220$_{2-n}$ to the capacitive element 120, i.e. will be indicative of the capacitance of the capacitive element 120. As this capacitance is a function of the level of the analyte of interest, the successive approximation code produced at the completion of the iterative process is therefore a digital representation of this level of the analyte of interest, e.g. of the relative humidity to which the sensor 200 has been exposed.

In summary, the controller 250 is responsible for iteratively enabling individual capacitive elements 120 and 220$_{2-n}$ of the charge scaling DAC 210 and to update the successive approximation register in response to the comparison result provided by the comparator 230. The comparison result may also be used to trigger the next iteration of the approximation instead of clock signal CLK.

In an embodiment, the N most significant bits of the ADC may be thermometer-coded. This may be implemented in any suitable manner. As such coding is known per se it will not be explained further for the sake of brevity.

FIG. 7 shows a simulation result of a capacitive sensing element 120 in an ADC of a successive approximation DAC designed in a CMOS 140 nm process. The variable Lfinger on the x-axis is a variable used to change the capacitance of the capacitive sensing element 120, which has been varied from 4-152% of the nominal capacitance of the MSB capacitor $220_1$. As can be seen from FIG. 7, a linear output response is obtained for the sensor 200 as a function of the capacitance of the capacitive sensing element 120 with a resolution of 0.3% per bit.

At this point it is noted that the use of a capacitive sensing element 120 is not limited to a binary-weighted ADC, but is equally feasible in e.g. a Golden Ratio Encoder, beta-encoder and so on.

The sensors 100 and 200 may be realized in any suitable manner. It is however preferable that the sensor of the present invention is monolithically integrated into an IC. More preferably, at least the capacitive elements 120 that are sensitive to the analyte of interest, e.g. moisture, are integrated in the back-end of the IC, such as in or on the metallization stack of the IC.

FIG. 8 schematically depicts an IC comprising a substrate 10 onto which a metallization stack is formed. Such a metallization stack typically comprises a stack of patterned metal layers 12 electrically insulated from each other by electrically insulating, i.e. dielectric layers 14. Metal portions in different metallization layers 12 may be conductively coupled to each other by means of vias 16 extending through dielectric layers 14 separating such metal portions from each other. The substrate 10 may be any suitable substrate material, e.g. single crystal Si, SiGe, silicon on insulator, and so on, and may carry a plurality of circuit elements such as transistors, diodes and so on.

Equally, the metallization stack may be formed in any suitable manner, and may contain any suitable number of metal layers 12 and dielectric layers 14. It should be understood that three metal layers are shown by way of non-limiting example only.

Each metal layer 12 and each dielectric layer 14 is depicted as a single layer in FIG. 2 for the sake of clarity only. It should be appreciated that such layers may consist of a number of stacked sub-layers, for instance in a submicron CMOS process, stacks of Ti, TiN, AlCu, TiN may be used to define a single metal layer in the metallization stack.

Each of the dielectric layers 14 may also comprise more than a single layer. For instance, such a dielectric layer may be a stack comprising FSG (fluorosilicate glass), $SiO_2$ and HDP oxide (High Density Plasma) any other suitable dielectric material combination. Other suitable materials may also be used.

Similarly, it will be apparent that the vias 16 may be formed from more than a single material. For instance, in the aforementioned CMOS 14 technology, a via 16 may be formed by a TiN liner and a W plug. Other semiconductor processes may use different materials, e.g. Cu for the metal layers 12 and vias 16. In FIG. 8, the common electrode 126, dielectric medium 124 and individual electrodes 122 are included in the metallization stack. It should be understood that the IC shown in FIG. 8 is not a completed device; further layers, e.g. a passivation layer (not shown) are usually formed over the metallization stack, e.g. to protect the IC from damage. Such further layers may be partially opened to expose the capacitive sensing elements 120 to the environment, i.e. to allow the analyte of interest to be absorbed by the dielectric medium 124.

It is equally feasible that the capacitive sensing array is formed on top of the metallization stack. This may be advantageous when the correct functioning of the metallization stack and/or underlying circuit elements may be comprised by exposure to the analyte of interest. This is for instance the case for immersion sensors where the large quantities of water can cause short circuits in the metallization stack and/or underlying circuitry. In such an embodiment, a moisture-impenetrable layer such a $Ta_2O_5$ layer may be formed between the capacitive sensing elements 120 and the metallization stack. Vias may be formed through the moisture-impenetrable layer to connect the electrodes of the capacitive sensing elements 120 to the underlying metallization stack and circuit elements.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention can be implemented by means of hardware comprising several distinct elements. In the device claim enumerating several means, several of these means can be embodied by one and the same item of hardware. The mere fact that certain measures are recited in mutually different dependent claims does not indicate that a combination of these measures cannot be used to advantage.

The invention claimed is:

1. A sensor for sensing an analyte of interest, the sensor comprising a plurality of capacitive elements, each capacitive element comprising a pair of electrodes separated by a dielectric medium wherein the dielectric constant of the dielectric medium of at least one of the capacitive elements is sensitive to the analyte of interest, the sensor further comprising:
    a comparator adapted to compare a selected set of said capacitive elements against a reference signal and to generate a comparison result signal, and
    a controller for selecting said set and for iteratively updating a digitized value indicative of a sensed level of the analyte of interest in response to said comparison result signal, wherein the sensor is arranged to output said value upon completion of said iteration; and
    wherein the dielectric medium of each of said capacitive elements has a dielectric constant dependent on a concentration of the analyte of interest in said medium, and wherein the controller is configured to select said set such that an overall capacity of the set remains constant.

2. The sensor of claim 1, wherein the plurality of capacitive elements comprises a first group of capacitive elements each having a first maximum capacity and a second group of capacitive elements each having a maximum capacity that is a multiple of the first maximum capacity.

3. The sensor of claim 1, wherein said plurality of capacitive elements defines a charge scaling digital-to-analog converter, wherein the plurality of capacitive elements comprises a single capacitive element having a dielectric medium with a dielectric constant sensitive to a level of the analyte of interest, said single capacitive element defining the most significant bit of the digital analog converter in an analog to digital conversion mode of the sensor,
    said plurality of capacitive elements further comprising a further capacitive element having a dielectric medium with dielectric constant insensitive to the analyte of interest, said further capacitive element defining the most significant bit of the digital analog converter in a programming mode of the sensor; and wherein the controller comprises a successive approximation register for providing a digital code.

4. The sensor of claim 3, wherein the highest N bits of the charge scaling digital-to-analog converter are thermometer-coded.

5. The sensor of claim 1, wherein the reference signal is a reference frequency signal.

6. The sensor of claim 1, wherein said capacitive elements have a common electrode.

7. The sensor of claim 1, wherein the analyte of interest is moisture.

8. An electronic device comprising the integrated circuit of claim 7.

9. An integrated circuit comprising the sensor of claim 1, wherein said capacitive elements are formed in or on the metallization stack of the integrated circuit.

10. The integrated circuit of claim 9, wherein at least one of the electrodes of said capacitive elements is formed in a metal layer of the metallization stack.

11. The integrated circuit of claim 9, wherein the capacitive elements are formed on said metallization stack, said integrated circuit further comprising a moisture barrier layer between the capacitive elements and the metallization stack.

12. A method of determining a level of an analyte of interest, comprising:

providing a plurality of capacitive elements, each capacitive element comprising a pair of electrodes separated by a dielectric medium wherein the dielectric constant of the dielectric medium of at least one of the capacitive elements is sensitive to the analyte of interest;

comparing selected set of said capacitive elements against a reference signal and generating a comparison result signal;

iteratively selecting said set in response to said comparison result signal; and generating a digitized signal indicative of the determined level of said analyte following completion of said iteration; and wherein:

the dielectric constant of the dielectric medium of each of said capacitive elements is sensitive to the analyte of interest;

said step of iteratively selecting said set comprises adjusting the number of capacitive elements in said set until said comparison result signal indicates a match between the aggregate capacitance of the capacitive elements in said set and the reference signal; and said step of generating the digitized signal comprises generating a signal indicative of the number of selected capacitive sensing elements following completion of said iteration.

13. The method of claim 12, wherein:

the dielectric constant of the dielectric medium of a single one of said capacitive elements is sensitive to the analyte of interest;

the plurality of capacitive elements defines a charge scaling digital-to-analog converter including said single capacitive element as the most significant bit in a digital to analog conversion mode and a further capacitive element having a dielectric medium with a dielectric constant insensitive to the analyte of interest as the most significant bit in a programming mode;

the method further comprises programming the digital-to-analog converter including the further capacitive element with a reference voltage in said programming mode;

reconfiguring the digital-to-analog converter by replacing the further capacitive element with said single capacitive element;

the step of iteratively selecting said set comprises sequentially selecting a single capacitive element of the digital to analog converter; and repeating the steps of:

comparing the charge stored on the selected capacitive element against the reference signal; and updating an successive approximation code in response to the generated comparison result signal;

until all capacitive elements of the digital-to-analog converter in the digital-to analog-conversion mode have been compared against the reference value; and wherein the step of generating the digitized signal comprises subsequently outputting the successive approximation code.

* * * * *